United States Patent [19]

Schwartz, deceased

[11] Plant 4,630

[45] Jan. 27, 1981

[54] ROSE PLANT

[75] Inventor: Ernest Schwartz, deceased, late of Kingsville, Md., by Hazel E. Schwartz, executrix

[73] Assignee: F. Harmon Saville, Nor'East Miniature Roses, Rowley, Mass.

[21] Appl. No.: 49,565

[22] Filed: Jun. 18, 1979

[51] Int. Cl.[3] ..... A01H 5/00

[52] U.S. Cl. ..... Plt./8

[58] Field of Search ..... Plt./3, 8–9

*Primary Examiner*—Robert E. Bagwill
*Attorney, Agent, or Firm*—Vincent G. Gioia

[57] ABSTRACT

A new off-white miniature rose of heavy petalage and blooming in large clusters.

1 Drawing Figure

The present invention relates to a new and distinct variety of rose plant of the miniature rose class, which was originated by my crossing as seed parent the rose known as "Charlie McCarthy" and an unknown seedling as pollen parent.

Among the novel characteristics possessed by this new variety which distinguish it from its parents and all other varieties of which I am aware are flowers of good petalage borne in large clusters (8 to 20 blooms per spray) and a vigorous, upright growth habit becoming lax with stem elongation, suitable for garden specimens or hanging baskets. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose producing large clusters of off-white blooms. The plants grow vigorously, making them useful in many gardening environments. Flowering is very profuse and repeats very fast. The glossy foliage is also very resistant to blackspot and mildew.

The accompanying drawing shows typical specimens of the vegetative growth and flowers of the new variety in different stages of development and is depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "158A" is plate 158A of the Royal Horticultural Society Color Chart.

Parentage: Seedling.

*Seed parent.*—"Charlie McCarthy".

*Pollen parent.*—"*Unknown Seedling*".

Class: Miniature.

The following observations are made of specimens grown in a greenhouse in Essex County, Mass., during the month of April.

1. FLOWER

Blooming habit: Profuse, continuous.

A. Bud:

(1) *Size.*—Small.

(2) *Form.*—Ovate.

(3) *Color.*—When sepals first divide — 158A. When petals begin to unfurl — 158C to D.

(4) *Sepals.*—Relatively short, smooth, not foliated.

(5) *Peduncle.*—Length — normal (½-inch). Aspect — straight. Strength — erect, supports blooms easily. Color — 145A.

B. Bloom:

(1) *Size.*—Average size when fully expanded — about ¾ to 1-inches.

(2) *Borne.*—Many flowered clusters and sprays from 8 to 20 blooms per spray.

(3) *Form.*—Cupped; opening flat.

(4) *Petalage.*—Number of petals under normal conditions — about 40 to 48.

(5) *Color.*—(During first two days). As flower opens color begins off-white generally from 158A as a bud and becoming 158C and 158D. Upon fully opening color becomes whiter, particularly at outer petals which tend to become 155B to 155D. The point of attachment of the petals remains off-white, generally 158B to 158C. Despite the off-white coloring evident close-up, the general tonality from a distance is white and the blooms seem to get whiter upon aging (155D).

C. Petals:

(1) *Texture.*—Relatively thin and soft.

(2) *Appearance.*—Inside — satiny; Outside — satiny.

(3) *Form.*—Wide and rounded, slight ruffle at edges; petals may reflex to point.

(4) *Arrangement.*—Regularly arranged, shingle-like.

(5) *Petaloids in center.*—Medium.

(6) *Persistence.*—Drop off cleanly.

(7) *Fragrance.*—Slight, spicy.

(8) *Lasting quality.*—Long lasting on plant and as cut flower.

2. REPRODUCTIVE ORGANS

A. Stamens, filaments and anthers:

(1) *Arrangement.*—Few.

(2) *Color.*—20B.

B. Pollen: Color — none.

C. Styles: Few, thin, uneven length.

D. Stigmas: Color — 145D.

E. Hips: None observed.

3. PLANT

A. Form: Originally upright, compact, but becoming lax with stem elongation.

B. Growth: Very vigorous, very free branching.
*Height attained.*—10-Inches high; 18-inches wide.

C. Foliage: Compound 5 to 7 leaflet leaves.
(1) *Size.*—Small.
(2) *Quantity.*—Abundant.
(3) *Color.*—New foliage: Upper side — near to 143A.Under side — near to 146C. Old foliage: Upper side — 137A. Under side — 139C.
(4) *Shape.*—Pointed, oval.
(5) *Texture.*—Upper side — very glossy. Under side — matte.
(6) *Edge.*—Serrated.
(7) *Serration.*—Not prominent.
(8) *Leaf stem.*—Color — near to 144A. Under side — 143C.
(9) *Stipules.*—Medium length, slightly bearded.
(10) *Resistance to disease.*—Blackspot — very good. Mildew — very good.

D. Wood:
(1) *New wood.*—Color — near to 143A. Bark — smooth.
(2) *Old wood.*—Color — near to 148A. Bark — smooth.

E. Thorns:
(1) *Thorns.*—Quantity: Few. On laterals from stalk — few. Form — short, pointed, curved downward and slanted downward. Length — medium short. Color (when young) — 195A. Position — irregular.
(2) *Prickles.*—None.

F. Winter hardiness: Needs some winter protection in worst winter areas.

I claim:

1. A new and distinct variety of rose plant of the miniature class, substantially as shown and described, characterized particularly by off-white to white blooms borne in many-flowered sprays on a vigorous plant quite resistant to mildew and blackspot.

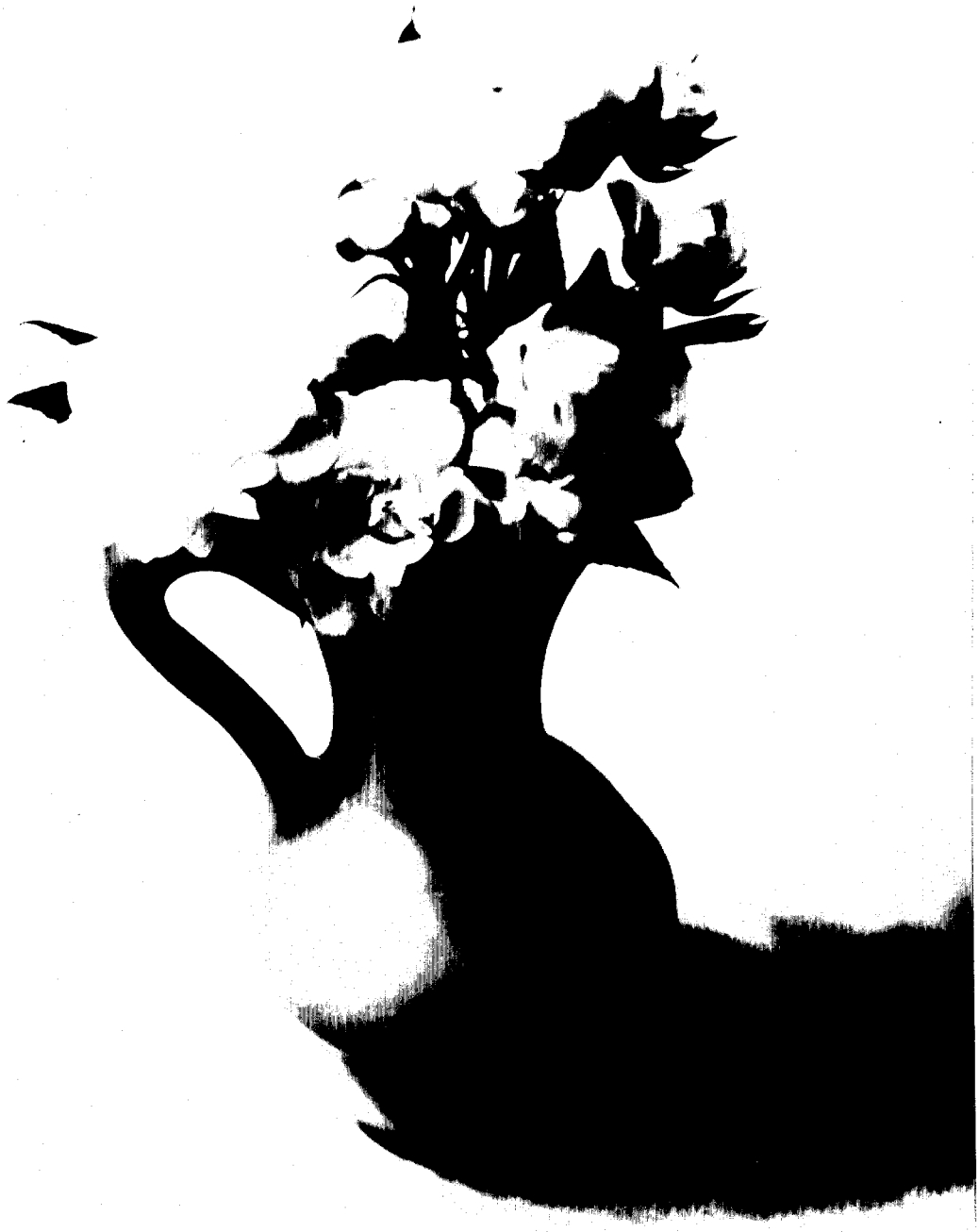

* * * * *